(12) United States Patent
Montano

(10) Patent No.: US 12,575,713 B2
(45) Date of Patent: Mar. 17, 2026

(54) OTOSCOPE SUCTION ADAPTER FOR REMOVING FOREIGN OBJECTS AND DEBRIS FROM THE EAR CANAL AND NASAL PASSAGE

(71) Applicant: Anthony Lee Montano, Brentwood, CA (US)

(72) Inventor: Anthony Lee Montano, Brentwood, CA (US)

( * ) Notice: Subject to any disclaimer, the term of this patent is extended or adjusted under 35 U.S.C. 154(b) by 999 days.

(21) Appl. No.: 17/306,818

(22) Filed: May 3, 2021

(65) Prior Publication Data

US 2022/0015610 A1 Jan. 20, 2022

Related U.S. Application Data

(60) Provisional application No. 63/051,911, filed on Jul. 15, 2020.

(51) Int. Cl.
| | |
|---|---|
| *A61B 1/00* | (2006.01) |
| *A61B 1/227* | (2006.01) |
| *A61B 1/233* | (2006.01) |

(52) U.S. Cl.
CPC ...... *A61B 1/00094* (2013.01); *A61B 1/00128* (2013.01); *A61B 1/00195* (2013.01); *A61B 1/227* (2013.01); *A61B 1/233* (2013.01)

(58) Field of Classification Search
CPC ............ A61B 1/00094; A61B 1/00128; A61B 1/00195; A61B 1/227; A61B 1/233
See application file for complete search history.

(56) References Cited

U.S. PATENT DOCUMENTS

| | | | | | |
|---|---|---|---|---|---|
| 5,658,235 | A | * | 8/1997 | Priest | A61B 1/227 |
| | | | | | 600/200 |
| 5,865,729 | A | * | 2/1999 | Meehan | A61B 17/42 |
| | | | | | 600/245 |
| 5,919,130 | A | * | 7/1999 | Monroe | A61B 1/042 |
| | | | | | 600/156 |
| 6,001,059 | A | * | 12/1999 | Elliott | A61B 1/00087 |
| | | | | | 600/184 |
| 6,306,084 | B1 | * | 10/2001 | Pinczower | A61B 10/0233 |
| | | | | | 600/184 |
| 8,876,707 | B2 | * | 11/2014 | Wellen | A61F 11/006 |
| | | | | | 600/199 |
| 2002/0038075 | A1 | * | 3/2002 | Tsai | A61B 1/0607 |
| | | | | | 600/130 |

(Continued)

*Primary Examiner* — Nicholas J Plionis
(74) *Attorney, Agent, or Firm* — West & Associates, A PC; Stuart J. West; Charlotte Rodeen-Dickert

(57) ABSTRACT

An otoscope suction adapter is a funnel shaped suction device that attaches to both an otoscope and suction unit in order to remove foreign objects and debris from the ear canal. The distal opening is referred to as the suction tip, which passes to a suction chamber, suction tube, and suction connector. On the posterior external aspect of the device, a point of attachment exists for the attachment of an otoscope. This allows for the transmission of light and visualization through the suction tip during suctioning procedures. The suction connector serves as a point of attachment for suction tubing and a portable or wall suction device. Emergency Room physicians affix this device to an otoscope and suction unit when attempting to remove foreign objects from a patient's ear canal. Practitioners may also use this device to remove excess ear wax and debris.

12 Claims, 4 Drawing Sheets

(56) References Cited

U.S. PATENT DOCUMENTS

| | | | | |
|---|---|---|---|---|
| 2011/0015489 | A1* | 1/2011 | Raghuprasad | A61B 1/227 |
| | | | | 600/187 |
| 2011/0295073 | A1* | 12/2011 | Truong | A61B 1/227 |
| | | | | 600/187 |
| 2012/0059224 | A1* | 3/2012 | Wellen | A61B 1/227 |
| | | | | 600/200 |
| 2013/0023914 | A1* | 1/2013 | Truong | A61B 1/015 |
| | | | | 606/162 |
| 2014/0336467 | A1* | 11/2014 | Eder | A61B 1/227 |
| | | | | 600/200 |
| 2016/0374546 | A1* | 12/2016 | Berbee | A61B 1/05 |
| | | | | 600/109 |
| 2017/0319188 | A1* | 11/2017 | Furlong | A61B 1/31 |
| 2018/0084999 | A1* | 3/2018 | Oved | A61B 1/00016 |
| 2019/0015254 | A1* | 1/2019 | Bendory | A61B 1/018 |
| 2019/0200850 | A1* | 7/2019 | Holland | A61B 1/07 |
| 2022/0167841 | A1* | 6/2022 | Keogh | A61B 1/04 |

* cited by examiner

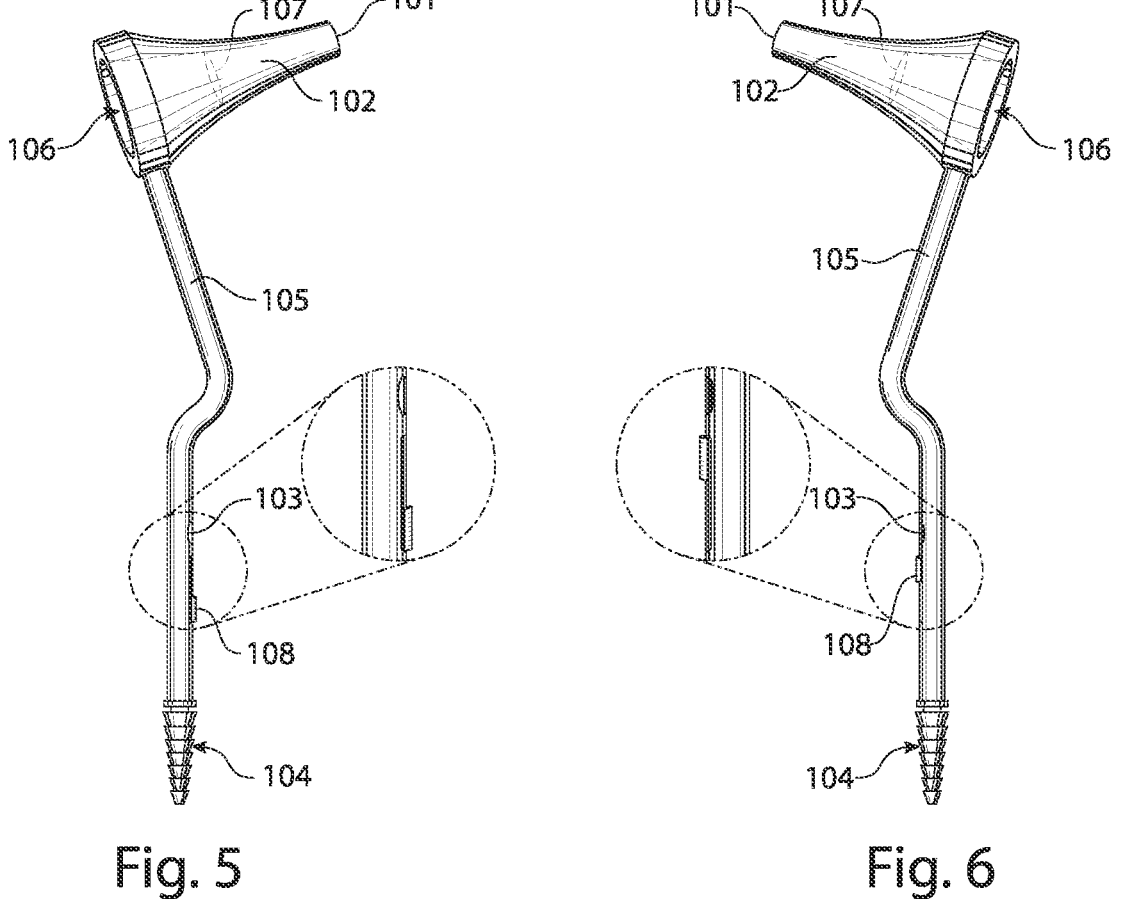
Fig. 5　　　　　　　　　　　　　　Fig. 6

OTOSCOPE SUCTION ADAPTER FOR REMOVING FOREIGN OBJECTS AND DEBRIS FROM THE EAR CANAL AND NASAL PASSAGE

CROSS-REFERENCE TO RELATED APPLICATION(S)

This application claims the benefit of priority of U.S. Provisional Patent Application 63/051,911, filed Jul. 15, 2020, the complete contents of which are hereby included by reference.

BACKGROUND

Technical Field

The present invention relates to otoscopes, particularly a suction adapter medical device used to remove foreign objects and debris from the ear canal and nasal passage.

Background

Emergency Departments frequently treat patients with foreign body obstructions of the ear canal and nasal passages. This occurs more frequently in pediatric patients but occurs in the adult population as well. Additionally, patients suffer temporary hearing loss due to debris and ear wax buildup in the ear canal. The current standard of practice for removing foreign objects and debris from the ear canal and nasal passage is both time consuming and painful.

Surgical suction instruments exist to remove foreign objects from the ear canal in a surgical setting and equipment sterilization is required prior to use. Lighted suction curette instruments exist that are impractical in the Emergency hospital setting. Such devices rely on small light source adapters and detachable magnification lenses that are likely to become lost or misplaced in the hectic Emergency environment, therefore rendering the remaining suction tips ineffective. These devices are more appropriate in the outpatient clinical office setting, but no practical or cost-effective suction device exists for removing foreign bodies or debris from the ear canal or nasal passage in the Emergency hospital setting.

The current method for removing foreign objects within the ear canal in the Emergency hospital setting involves the use of a long plastic or metal curette device which is passed into the ear canal in an effort to dislodge and remove the foreign object. This method causes discomfort to the patient and proves to be a traumatic experience for younger patients. Additionally, this method may cause damage to the ear drum while attempting to pass the curette behind the foreign object in an effort to remove it, especially in younger patients who may be unable to remain still during the procedure. In some instances, the object is unable to be removed using this method and a specialty consult is required. A specialty consult results in a longer hospital stay and increased costs to the patient. A curette device is also used to remove ear wax and debris from the ear canal, which may again cause discomfort for the patient.

The current method for removing foreign objects from the nasal passages in the Emergency hospital setting involves the use of a nasal speculum used to hold open the affected nostril, while simultaneously passing a large metal forceps into the nasal passage and grasping the foreign object. This method causes great discomfort and proves to be a traumatic experience for younger patients.

An otoscope is a device that allows practitioners to shine light into the ear canal, while simultaneously observing the ear canal through a magnification lens. Otoscopes provide the light source and magnification required to adequately visualize the ear canal and nasal passage, but do not provide a means for removing foreign objects or debris without the need for a separate medical device.

Suction adapters commonly found in the Emergency hospital setting are not designed to safely remove objects from the ear canal or nasal passage due to their large size and shape. These suction devices also do not provide the light source or magnification needed to visualize the foreign object or debris within the ear canal or nasal passage. Without proper visualization, damage to the eardrum and other structures may occur.

A need exists for an otoscope adapter that reduces patient discomfort, while allowing for simultaneous visualization and suctioning of the ear canal and nasal passage. The present invention relates to an otoscope suction adapter that addresses drawbacks associated with the current standard of practice for removing foreign objects and debris from the ear canal and nasal passages.

SUMMARY

The present invention seeks to provide a solution to this problem(s) by providing an otoscope suction adapter that can be easily affixed to an otoscope, suction tubing, and a portable or wall suction unit. The use of suction allows for the removal of foreign objects and debris from the ear canal and nasal passage without the need for a prolonged and painful procedure.

The adapter is attached to an otoscope, allowing for increased control of the suction tip upon insertion and throughout the duration of the procedure. By attaching the suction adapter to an existing otoscope, light and magnification are applied through the attachment in order to provide visualization of the ear canal and nasal passage during suctioning procedures. By using an otoscope, a piece of durable medical equipment found in most clinical settings, there is no need to manufacture the device with a separate light source or magnifying lens.

Once affixed to the otoscope, suction tubing is attached to the device. Suction tubing is then attached to a portable or wall suction unit. The portable or wall suction unit is then turned on to the continuous suction setting. The tip of the suction device is then inserted into the ear canal or nasal passage, where practitioners can observe foreign objects and debris within the ear canal and nasal passage. Through the use of a suction control port on the device, practitioners are able to control whether or not suction is applied to the device. In doing so, practitioners are able to reduce the risk of injury to structures of the ear canal and nasal passages during suctioning procedures by only applying suction when necessary.

BRIEF DESCRIPTION OF THE DRAWINGS

Further details of the present device are explained with the help of the attached drawings in which:

FIG. 5 illustrates another embodiment of the present device as viewed from a first side.

FIG. 6 illustrates another embodiment of the present device shown in FIG. 5 as viewed from a second side.

DETAILED DESCRIPTION

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Figure 1:
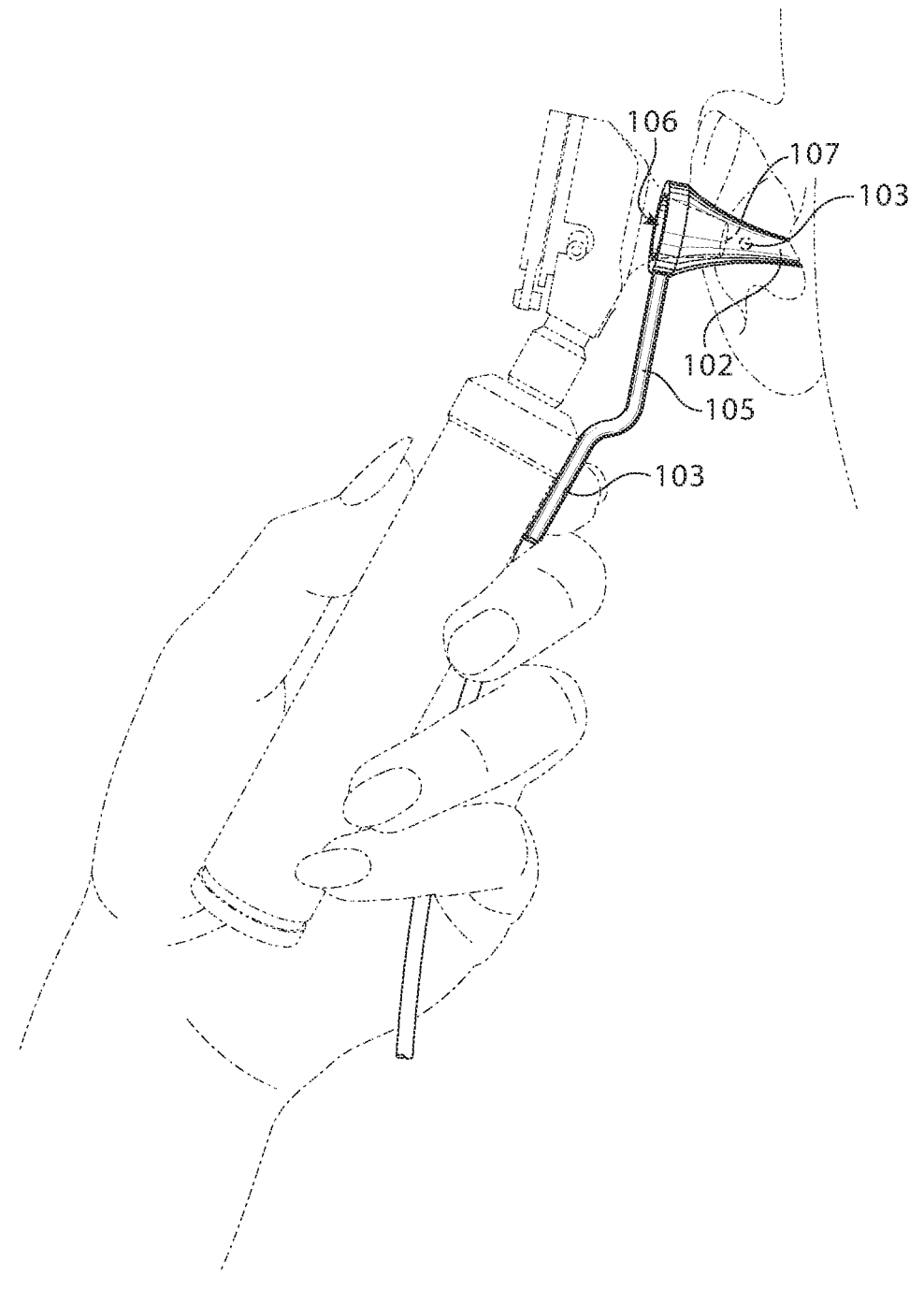
FIG. 1 illustrates a perspective drawing of an embodiment of an otoscope suction adapter, attached to an otoscope and inserted into the ear canal, according to the present invention.

FIG. 1 illustrates a perspective drawing of an embodiment of an otoscope suction adapter, attached to an otoscope and inserted into the ear canal, according to the present device. A suction chamber 102 can have a substantially conical geometry or any other known and/or convenient configuration. The distal end of a suction chamber 102 can be open and terminate in a suction tip 101.

The proximal end can comprise an otoscope connector 106, which can hold an otoscope suction adapter in place. In such embodiments, an otoscope connector 106 can be comprised of an open-ended substantially conical member, the proximal end of which can selectively engage with the distal end of an otoscope and lock in place via friction fit or any other known and/or convenient method. In some embodiments, an otoscope connector 106 can twist onto an otoscope and be locked into place by the presence of a small tab within a suction chamber 102 that can lock into a groove found on an otoscope.

In some embodiments, an otoscope connector 106 can be aligned substantially coaxially with the central longitudinal axis of a suction chamber 102, but in other embodiments can have any other known and/or convenient configuration. In such embodiments, the proximal end of an otoscope connector 106 can be substantially coincident and integrated with the proximal end of a suction chamber 102. However, in other embodiments, an otoscope connector 106 can be removably connected with a suction chamber 102/

In some embodiments, an otoscope connector 106 can be made of a substantially transparent rigid polymer. In other embodiments a connector 106 can be made of metal, rubber, or any material known and/or convenient that is commonly used in manufacturing medical devices. In other embodiments an otoscope connector 106 can be held in place by the user, physically securing an otoscope connector 106 against an otoscope by manual pressure or by the application of a strap or other known and/or convenient securement device that attaches to both an otoscope connector 106 and an otoscope.

The distal end of an otoscope connector 106 can comprise a substantially transparent lens 107 that can permit light to pass through the device and allows visualization through a suction chamber 102. In some embodiments a lens 107 can be comprised of a substantially transparent rigid polymer. In other embodiments a lens 107 can be comprised of glass or any other known and/or convenient substantially transparent material that allows for the passage of light and through which a user can observe structures of the ear canal and nasal passage.

In some embodiments, a suction tube 105 can be attached to a suction chamber 102 and allow for fluid communication, as well as air, debris, and foreign objects to pass through the device. A suction tube 105 can have a substantially circular cross-section or any other known and/or convenient geometry. In some embodiments, a suction tube 105 can be made of a substantially transparent rigid polymer, but in other embodiments a suction tube 105 can be made of a flexible rubber material, other polymer, metal, or any other known and/or convenient material commonly used in manufacturing medical devices.

In some embodiments, when in use, a suction tube 105 can run substantially parallel to an otoscope handle, but in other embodiments can be placed in any other known and/or convenient location or configuration. In other embodiments a suction tube 105 can attach at the top, side, or any other portion of a suction chamber 102 and can be of any known and/or convenient size and geometry. In some embodiments a suction control port 103 can be positioned near the proximal end and on the anterior surface of a suction tube 105. The user of the device can cover and uncover a port 103 with an index finger in order to control the suction that can be applied to the device, In other methods, a user may also cover a port 103 with any other finger or device that is able to form a seal over the port 103. When a port 103 is covered, suction is applied to the device. When a port 103 is uncovered, no suction is applied to the device. In other embodiments in which a suction tube 105 is placed elsewhere along the suction chamber, a suction control port 103 may no longer be found on a suction tube 105 and instead be positioned on the suction chamber 102 at any known and/or convenient position along the perimeter of a suction chamber 102. (Shown as an optional feature by dotted line in FIG. 1.)

Figures 2, 3:
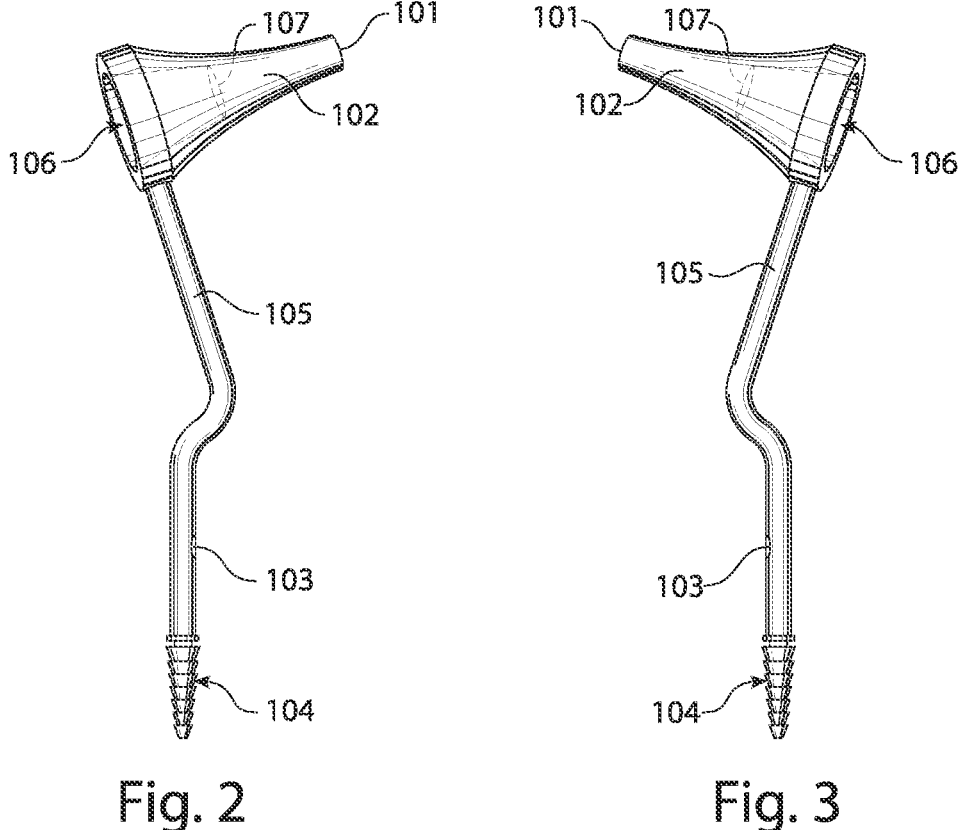
FIG. 2 illustrates an embodiment of the present device as viewed from a first side.
FIG. 3 illustrates an embodiment of the present device shown in FIG. 2 as viewed from a second side.

FIG. 2 illustrates an embodiment of the present device as viewed from a first side. FIG. 3 illustrates an embodiment of the present device as viewed from an opposite second side. The proximal end of a suction tube 105 can comprises a suction connector 104 that can act as a point of attachment for suction tubing, which can then be attached to a portable or wall suction unit. As shown in FIGS. 2 and 3, a suction connector 105 can comprise a series of circumferential ridges to removably connect to suction tubing, but in other embodiments can use any other known and/or convenient connecting configuration or device.

When a suction unit is turned on, an otoscope suction adapter can then provide suctioning capabilities only when a suction control port 103 is covered by a user. Continuous suctioning without visualization can cause damage to the structures of the ear. Therefore, a port 103 should be left uncovered until a user is ready to suction foreign objects or debris from the ear canal or nasal passage. In a preferred embodiment, a suction connector 104 can be made of a rigid plastic, but in other embodiments a connector 104 can be made of metal, rubber, or any other known and/or convenient material commonly used in manufacturing medical devices.

At the distal end of an otoscope suction adapter can be a suction tip 101, which can be inserted into a patient's ear to remove foreign objects and debris during suctioning. In some embodiments the outer diameter of a tip 101 can be in the range of 4.0 mm±0.5 mm, but in other embodiments, the outer diameter of a tip 101 can be in the range from 6.5 mm±5.5 mm. In some embodiments, a suction tip 101 can be made of a substantially transparent rigid polymer, but can also be made of metal, rubber, or any other known and/or convenient material commonly used in manufacturing medical devices. A suction tip 101 can be lined and covered with a soft polymer material to improve patient comfort and form a seal during the removal of large foreign objects during suctioning.

Debris and foreign objects removed during suctioning can pass through a suction tip 101, a suction chamber 102, and can then be carried away from a suction chamber 102 by a suction tube 105 and out through a suction connector 104. In some embodiments a suction tube 105 can connect a suction chamber 102 to a connector 104. In other embodiments a suction chamber 102 can be connected directly to a suction connector 104 without the use of a suction tube 105, with the suction control port 103 located on a suction chamber 102 and providing for a more compact device that can fit a larger variety of otoscopes. In other embodiments, a suction tube 105 can be coiled around a suction chamber 102 with a suction control port 103 placed somewhere along that coil.

In one embodiment, an otoscope suction adapter can attach to an otoscope at the site of an otoscope connector 106, however it is understood that practitioners can independently elect to use the adapter without the presence of an otoscope. This method of use can include using the suction adapter as a standalone device in which the user can attach suction tubing 105 to a suction connector 104 and applies suction to the ear canal and nasal passages without the use of an otoscope.

Figure 4:
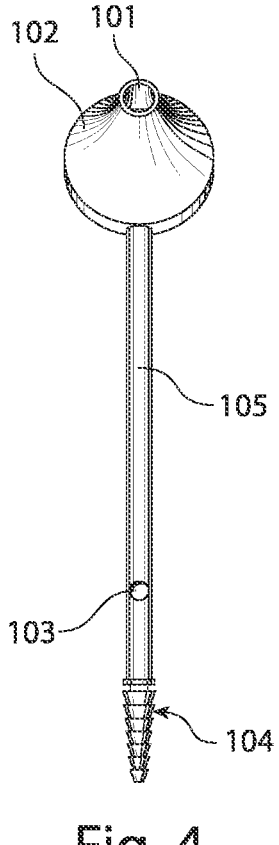
FIG. 4 illustrates an embodiment of the present device as viewed from the front.

FIG. 4 illustrates an embodiment of the present device as viewed from the front. A substantially circular suction tip 101 can form the distal opening of a suction chamber 102. A chamber 102 can be a substantially conical portion of the device that can allow for easy insertion of the present device into the ear canal and nasal passage. A substantially vertical suction tube 105 can form the connection between a suction chamber 102 and a suction connector 104. A suction control port 103 can be found along the anterior surface of a suction tube 105. The suction control port 103 allows the user to control whether or not suction is applied to the device.

One embodiment of the present device can be made of substantially transparent, rigid polymer, plastic, metal, rubber, or any other known and/or convenient material used in manufacturing medical devices. It can also be made by using a variety of materials for each of the listed components.

FIG. 5 depicts a first side view of another embodiment of the present device. FIG. 6 depicts this embodiment as seen from an opposite second side. In the embodiment shown, a port 103 can further comprise an incremental control device 108. As shown in FIGS. 5 and 6, an incremental control device 108 can be a slider mechanism, but in other embodiments can be any other known and/or convenient device, Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed:

1. An otoscope suction device comprising:
a suction chamber having a proximal end and a distal end;
a suction tip at the distal end of said suction chamber;
a suction tube having a proximal end and a distal end, wherein said distal end of said suction tube is connected to the proximal end of said suction chamber such that there is fluid communication between said suction chamber and said suction tube, and wherein the proximal end of said suction tube terminates in a suction connector device;
a port;
an otoscope connector having a proximal end and a distal end, wherein said proximal end of said otoscope connector is adapted to selectively engage with the distal end of an otoscope such that the distal end of said otoscope connector is positioned anterior to the junction of the distal end of the suction tube and the proximal end of said suction chamber; and
a lens located at the distal end of said otoscope connector.

2. The device of claim 1, wherein said suction chamber and said otoscope connector have a substantially conical geometry configured to at least partially enter an ear canal.

3. The device of claim 2, wherein said suction chamber and said otoscope connector are coaxially aligned with the central longitudinal axis of said suction chamber.

4. The device of claim 3 wherein said suction chamber and said otoscope connector are coincident and at least partially integrated at their proximal edges.

5. The device of claim 3, wherein said suction chamber and said otoscope connector are coincident and removably connected at their proximal edges.

6. The device of claim 3 wherein said port is located on the anterior surface of said suction tube.

7. The device of claim 3, wherein said port is located on said suction chamber.

8. The device of claim 3, wherein said suction chamber and said otoscope connector are comprised of a rigid polymer.

9. The device of claim 8, wherein said rigid polymer is at least partially transparent.

10. The device of claim 8, wherein said suction tube is comprised of a rigid polymer.

11. The device of claim 10, wherein said rigid polymer is at least partially transparent.

12. The device of claim 8, wherein said suction tube is comprised of a flexible polymer.

* * * * *